United States Patent [19]

Gazzi

[11] Patent Number: 4,657,571
[45] Date of Patent: Apr. 14, 1987

[54] PROCESS FOR THE RECOVERY OF HEAVY CONSTITUENTS FROM HYDROCARBON GASEOUS MIXTURES

[75] Inventor: Luigi Gazzi, Milan, Italy
[73] Assignee: Snamprogetti S.p.A., Milan, Italy
[21] Appl. No.: 746,331
[22] Filed: Jun. 19, 1985
[30] Foreign Application Priority Data Jun. 29, 1984 [IT] Italy ............................... 21652 A/84
Oct. 24, 1984 [IT] Italy ............................... 23287 A/84

[51] Int. Cl.⁴ .............................................. F25J 3/00
[52] U.S. Cl. ........................................... 62/17; 62/23; 62/27; 62/38; 62/39
[58] Field of Search ................... 62/11, 17, 23, 27, 38, 62/39

[56] References Cited

U.S. PATENT DOCUMENTS

| | | | |
|---|---|---|---|
| 4,155,729 | 5/1979 | Gray et al. | 62/38 |
| 4,203,741 | 5/1980 | Bellinger et al. | 62/23 |
| 4,272,269 | 6/1981 | Hammond et al. | 62/17 |
| 4,444,577 | 4/1984 | Perez | 62/39 |
| 4,486,209 | 12/1984 | Fabbri et al. | 62/39 |
| 4,488,890 | 12/1984 | Foerg et al. | 62/17 |
| 4,509,967 | 4/1985 | Sweet | 62/17 |

Primary Examiner—Ronald C. Capossela
Attorney, Agent, or Firm—Morgan & Finnegan

[57] ABSTRACT

A process is disclosed for the recovery of heavy constituents from high-pressure hydrocarbon gaseous mixtures comprising the steps of first cooling and partially condensing the gaseous mixture. The condensed liquid is then separated and fed to a fractionation column while the remaining non-condensed gaseous mixture is subject to turboexpansion. The liquid condensed on turboexpansion is then separated and fed to the fractionation column where the heavy constituents are recovered. The gases streaming from the fractionation column and those separated by turboexpansion are compressed, separately or together, up to the consignment pressure of the treated gas. This process is characterized in that the liquid condensed on turboexpansion is separated in a separator-absorber wherein, in addition to the condensed liquid, a liquid obtained by the absorption of the non-condensed heavy constituents is collected. Absorption is accomplished by an absorbent hydrocarbon oil, substantially free from the heavy constituents to be recovered. This oil is obtained from the cooling and partial condensation of the gases streaming from the fractionation column wherein a portion of the heavy constituents are removed by means of a dephlegmator and substantially compressed to a pressure higher than the pressure of the fractionation column.

18 Claims, 5 Drawing Figures

PROCESS FOR THE RECOVERY OF HEAVY CONSTITUENTS FROM HYDROCARBON GASEOUS MIXTURES

The present invention relates to a process for recovering heavy components from hydrocarbon gaseous mixtures. Many processes are already known for the recovery of heavy components from gaseous mixtures, among which the turbo-expansion ones are more and more frequently used. They consist essentially in producing the cooling necessary for the condensation and for the fractionation of said heavy constituents by expanding the raw gas in a turbine, i.e., with the production of external work, and compressing again the treated gas.

The main reason for which the turbo-expansion processes have been so largely adopted consists in that, as the cooling fluid coincides with the main process stream, all the equipment constituting the cooling cycle can be eliminated, thus largely reducing in this way the investment costs.

Obviously, the elimination of the equipment of the cooling cycle hereinabove mentioned relates to all the accessory equipment, not to the compressor of the cycle, which is not elminated, but replaced by the compressor of treated gas.

This means that the investment for such equipment as vessels, heat exchangers, etc., is largely reduced, whilst the cost of compressors is not changed to any notable extent. The compression station of the treated gas becomes hence of a particular importance as for the cost of a turbo-expansion plant, up to reaching in some cases one half of the overall investment.

It is hence of the highest importance, to the purpose of reducing both the operating costs and the installation investments to reduce, with all other conditions being the same, the recompression power. A flowsheet of a turbo-expansion plant quite usual in the known art is represented in FIG. 1. The raw gas, preliminarily dried, enters the plant through the pipe 1, is cooled by means of process streams in the exchangers 2, 3 and 4 and is sent into the vessel 5, wherein the condensed liquids are separated. Said condensed liquids 6 are expanded by means of the valve 7 into the separator 8, whilst the gas 9 streaming from the separator 5 is expanded in the turbo-expander 10 and is fed to the separator 11, wherein from the gaseous phase 14 the formed liquid phase is separated (12), which is sent to the separator 8 by means of the valve 13.

From the separator 8 a liquid stream 15 is drawn, which is fed to the fractionation column 17 through the valve 16.

Inside the column 17 the heavy constituents are fractionated from residual gas, and they leave the plant by means of the pipe 18. Said fractionation column is provided with the reboiler 19, with the intermediate reboiler 3 and with the dephlegmator 20, cooled by the gas (14) separated in 11. The gas 21 streaming from the top of the column 17 is combined with that (22) outcoming from the separator 8, is heated in the exchanger 4, is compressed by the compressor 23, is cooled in 24 and is combined with the main gas stream inside the pipe 25. The fuel gas necessary for the operation of the plant is diverted under a suitable pressure by the pipe 26.

The main gas stream 14, outcoming from the separator 11, is heated in the dephlegmator 20 and in the exchanger 2, is compressed in the compressor 27, driven by the turbo-exchanger 10, then in the compressor 28, actuated by an independent driving unit, and is finally cooled in 29 before leaving the plant through the pipe 30.

The flowsheet according to the known art has been applied to the recovery of LPG from natural gas. As in this case the required propane level in LPG is very low, the key component is butane.

The incoming gas is supplied at 35° C. and under 70.3 kg/cm$^2$ and has the following molar composition:

| | |
|---|---|
| $N_2$ | 18.65 kmol/h |
| $CO_2$ | 109.37 kmol/h |
| $C_1$ | 11521.08 kmol/h |
| $C_2$ | 529.83 kmol/h |
| $C_3$ | 157.92 kmol/h |
| $IC_4$ | 40.15 kmol/h |
| $NC_4$ | 44.13 kmol/h |
| $IC_5$ | 21.15 kmol/h |
| $NC_5$ | 15.41 kmol/h |
| $NC_6$ | 29.10 kmol/h |
| $NC_7$ | 10.89 kmol/h |
| $NC_8$ | 5.61 kmol/h |
| $NC_9$ | 2.01 kmol/h |
| $NC_{10}$ | 0.76 kmol/h |
| Total | 12506.06 kmol/h |

The raw gas arrives at the separator 5 at −39° C. and is further cooled to −72° C. by turbo-expansion to 35 kg/cm$^2$. The liquids obtained in the separators 5 and 11 are fractionated in the column 17, from whose bottom a $C_{3+}$ liquid product is obtained, which is suitable to be fractionated into LPG of desired specification and into gasoline.

The residual gas is recompressed to 71 kg/cm$^2$, after having diverted the fuel gas, the heavy hydrocarbons, recovered as liquid from the bottom of column 17, have the following molar composition:

| | |
|---|---|
| $C_3$ | 39.45 kmol/h |
| $IC_4$ | 33.55 kmol/h |
| $NC_4$ | 42.11 kmol/h |
| $IC_5$ | 21.13 kmol/h |
| $NC_5$ | 15.40 kmol/h |
| $C_6$ | 29.09 kmol/h |
| $C_7$ | 10.89 kmol/h |
| $C_8$ | 5.61 kmol/h |
| $C_9$ | 2.01 kmol/h |
| $C_{10}$ | 0.76 kmol/h |
| Total | 196.47 kmol/h |

The total recovery of $C_4$ in the liquid product is of 89.77% relatively to $C_4$ contained in the raw gas. The powers used for the recompression of the gas are:

| | | |
|---|---|---|
| Compressor | 23 | 552 kW |
| | 28 | 7476 kW |
| Total | | 8028 kW |

In the total, the power of the compressor 27 (absorbed power 2055 kW) has not been taken into account, in that it is driven by the turbo-expander and it therefore does not contribute to the consumptions.

The basic drawback of the known art consists in that the recovery of heavy constituents is carried out in a single equilibrium step, which is accomplished at the outlet of the turbo-expander (in the flowsheet of FIG. 1 in the separator 11). This involves the fact that, in order to achieve the recovery of the heavy components to the required extent, very low temperatures must be reached, and it is hence necessary to expand to low pressures, with consequent very large recompression powers.

It is on the other hand difficult to carry out the separation in two or more equilibrium steps, e.g., in a distillation column or at least in a rectification vessel, in that in a turbo-expansion plant the turbo-expanded gas, which should constitute the feed for the rectification vessel, is also the coldest stream of the plant, from which substantial amounts of refrigeration units can be obtained, so that the possibility is lacking of cooling the head condenser of the hypothetical rectification vessel. It has been realized in the past a rectification vessel cooled by means of the liquid separated in the separator 11, expanded to a lower pressure; but the useable refrigerating units are too few and the rectification vessel is therefore ineffective.

We have found that it is possible to produce a hydrocarbon liquid to be used in a column of more than one equilibrium step for the further fractionation of the main stream gas downstream of the turboexpander starting from gaseous streams lean of the key constituent to be recovered, which, relatively to the main gas stream are:
either under a higher pressure
or heavier (i.e. in the average less volatile) and under a higher pressure.

The column of more than one equilibrium step takes the form of an absorber. It has been found that its function is highly positive in that it allows it to operate at higher temperatures, and hence under higher pressures, at the outlet of the turbo-expander, thus allowing considerable savings in the end recompression.

The process being the object of the present invention for the recovery of heavy constituents from a high-pressure hydrocarbon gaseous mixture comprises the following steps:
(a) cooling and partial condensation of the hydrocarbon gaseous mixture;
(b) separation of the condensed liquid from the gaseous mixture and feeding of the same to a fractionation column;
(c) turbo-expansion of non-condensed gaseous mixture;
(d) separation of the liquid condensed on turbo-expansion, and feeding of the same to the said fractionation column from whose bottom the heavy constituents are recovered;
(e) recompression both of the gases streaming from the fractionation column and of the gases separated in step (d), separately or together, up to the consignment pressure of treated gas
characterized in that the separation of the liquid condensed on the turbo-expansion of the gaseous mixture is carried out in a separator-absorber in whose lower portion in addition to the condensed liquid a liquid is collected which is obtained by the absorption of non-condensed heavy constituents by means of an absorbent oil constituted by a hydrocarbon oil, substantially free from the heavy constituents to be recovered, obtained from the cooling and from the at least partial condensation of the gases streaming from the fractionation column, previously deprived of at least a portion of the heavy constituents by means of a dephlegmator with which the same fractionation column is provided, said gases streaming from the fractionation column, upstream or downstream of the dephlegmator are compressed to a higher pressure than that of the fractionation column.

The pressure at the outlet of the turbo-expander and the pressure of the absorber are comprised within the range of from 5 to 70 atm, preferably of from 15 to 50 atm, whilst the fractionation column operates under a pressure comprised within the range of from 5 to 45 atm, preferably of from 8 to 35 atm.

If also the recovery of ethane is required, it is necessary that the pressure of the gas from which the absorbent liquid is condensed be higher than the pressure of the absorber, which can be obtained by pumping into the fractionation column the liquid condensed on turbo-expansion under a pressure higher than that of the separator-absorber.

Instead of pumping the liquid condensed on the turbo-expansion to a pressure higher than that of the separator-absorber into the fractionation column, it is possible to partly draw from a suitable point of the recompression unit as per the step (e) the gases streaming from the fractionation column together with the gases separated in step (d) in order to subsequently cool and condense them at least partially, obtaining from them the absorbent liquid under a pressure higher than that of the absorber.

Before being cooled and condensed the gases drawn from the suitable point of the recompression unit can be possibly further compressed.

The pressure of said gases is comprised within the range of from 20 to 200 atm, preferably of from 35 to 80 atm.

The liquids obtained from the turbo-expansion and from the absorption with hydrocarbon oil can be possibly stripped with gas before being sent to the fractionation column.

The stripping gas may also be the raw gas at the inlet of the plant, preferably in an amount comprised within the range of from 2 to 25% by volume relatively to the total amount of the said raw gas.

A portion of the stripping gas drawn from the inlet of the plant may be replaced with hydrocarbon vapours generated in a reboiler.

The invention shall now be better disclosed by taking advantage of the flowsheets of FIGS. 2, 3, 4 and 5, which represent preferred embodiments, but which must not be considered as limitative of the same invention.

Figure 1:
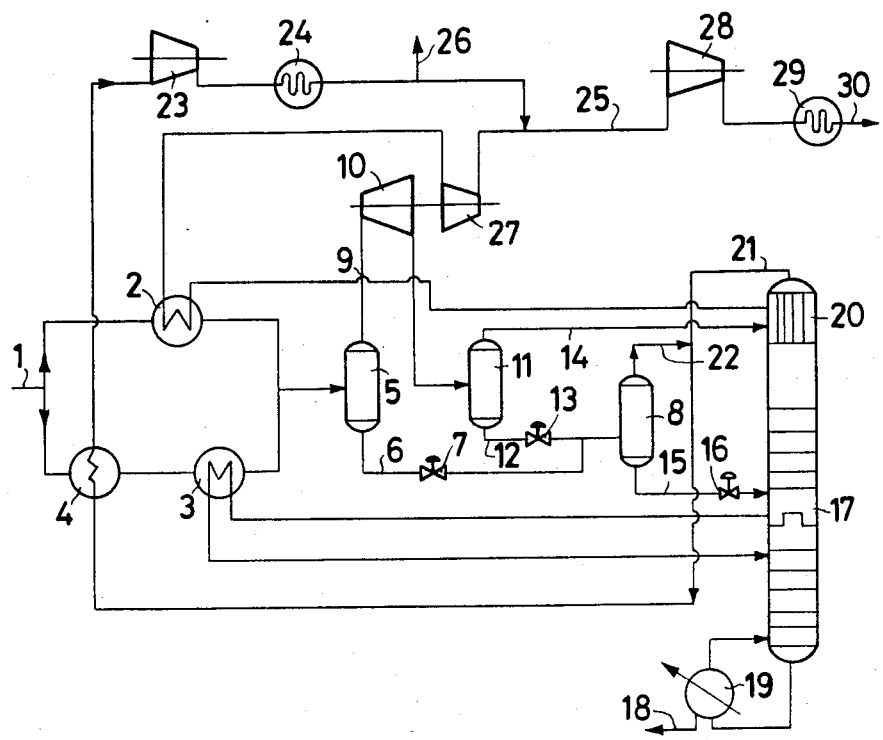
FIG. 1 shows a schematic of a prior art device.
Figure 2:
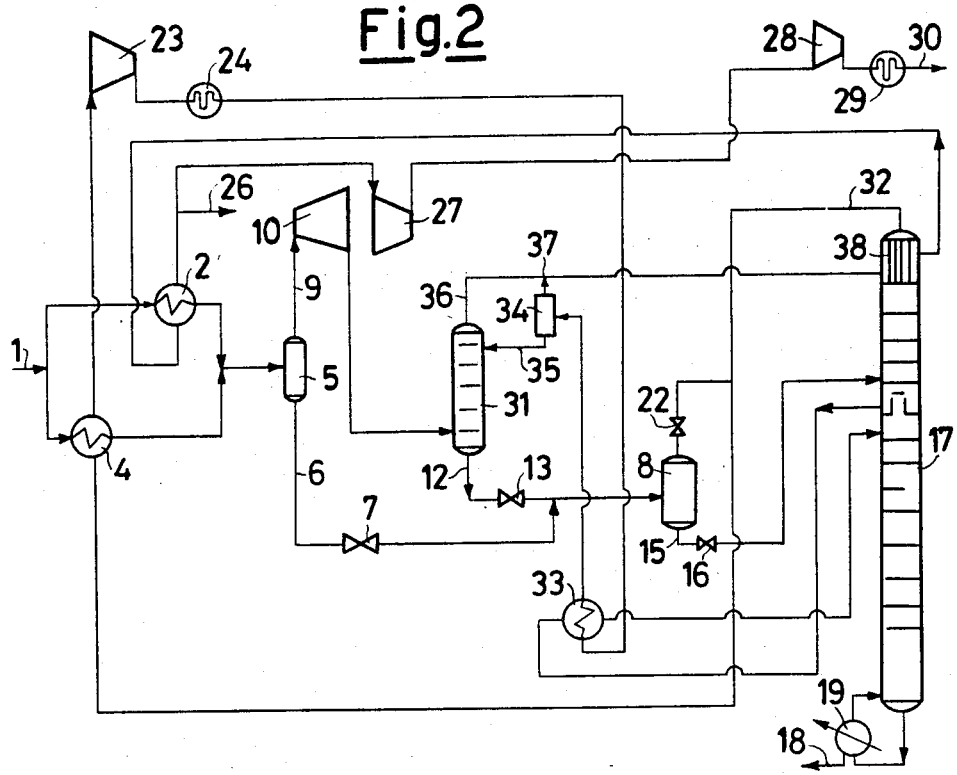
FIG. 2 shows a schematic of a device of one embodiment of the present invention.

In FIG. 2, the raw gas, previously dried, in a similar way to the flowsheet of FIG. 1, enters the plant through 1, is cooled by means of process streams in the exchangers 2 and 4 and is sent to the separator 5 separating the condensed liquids 6, which are expanded in 7 and sent to the separator 8, and the gas 9 which is in its turn expanded in the turbo-expander 10.

From the separator 8 a liquid stream 15 is drawn, which through the valve 16 is sent to the fractionation column 17.

The turbo-expanded gas is fed to the absorber 31, wherein it is washed in countercurrent with a liquid produced by partly condensating the head gases 32 of the column 17 in the exchanger 33, after that to them the gases outcoming from the separator 8 through the valve 22 have been added amd after that the resulting stream has been heated in the exchanger 4, compressed in 23 and cooled in 24. The condensed liquid is separated in the vessel 34 and is sent to the absorber 31 by means of the pipe 35. The gas separated in 34 is combined with the gas 36 outcoming from the absorber 31 via the pipe 37, the gaseous mixture formed being then heated in the dephlegmator 38 and in the exchanger 2, before being compressed in 27 and 28, cooled in 29 and sent to the distribution network through 30.

The liquid 12 streaming from the absorber 31 is sent to the separator 8 through the valve 13. The heavy constituents leave the plant through the pipe 18, whilst the fuel gas is derived by means of the pipe 26.

The column 17 is provided with the reboiler 19, with the intermediate reboiler 33 and with the dephlegmator 38.

The flowsheet of FIG. 2 is well suited to the recovery of $C_3$ or of still heavier fractions. If also the recovery of ethane is required it is needed, as previously stated, that the gas from which the absorbent liquid is condensed, be at a pressure higher than that of the absorber. This can be accomplished, always to non limitative exemplifying purposes, by means of the flowsheet of FIG. 3. The gas turbo-expanded in 10 as is usually fed to the absorber 31. From here the bottom liquid 39 to which the liquid separated in 5 is added through the valve 7, is pumped by means of the pump 40 into the column 17.

The head gas 32 of the column 17 is partly condensed in the exchanger 41, consuming the refrigeration units of the treated gas 36, and is separated in 42; the liquid 43 goes to the absorber through the valve 44, whilst the gas 45, after having been heated in the exchanger 4, is sent to a suitable point of the compression unit, e.g. to an intermediate intake of the compressor 28.

Figure 3:
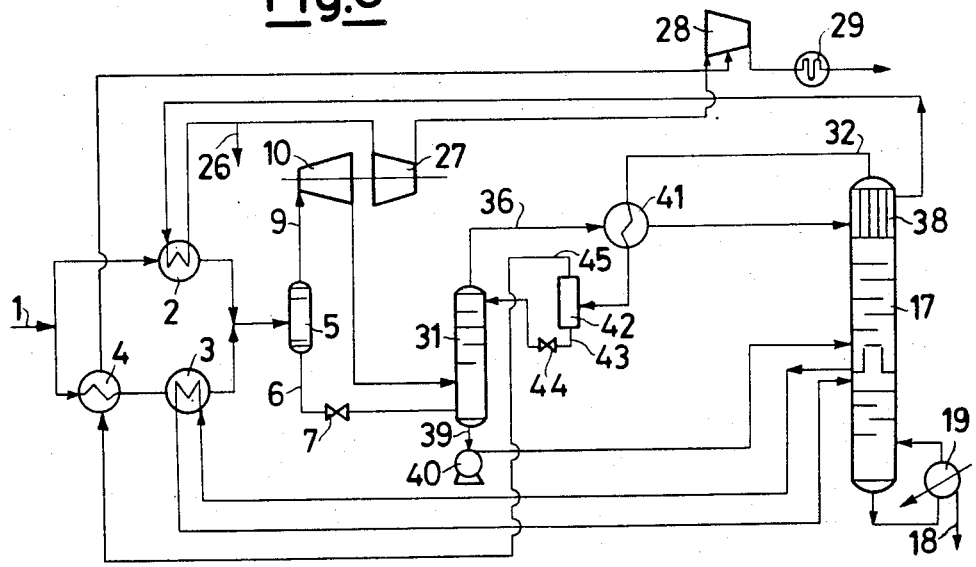
FIGS. 3-5 show a schematic of a device of alternative embodiments of the present invention.

As an alternative to the flowsheet of FIG. 3, the gas to be liquified may be drawn from the delivery of the compressor 28, or it can be even necessary to further compress the gas to be liquified, up to a pressure higher than that of consignment of treated gas.

Figure 4:
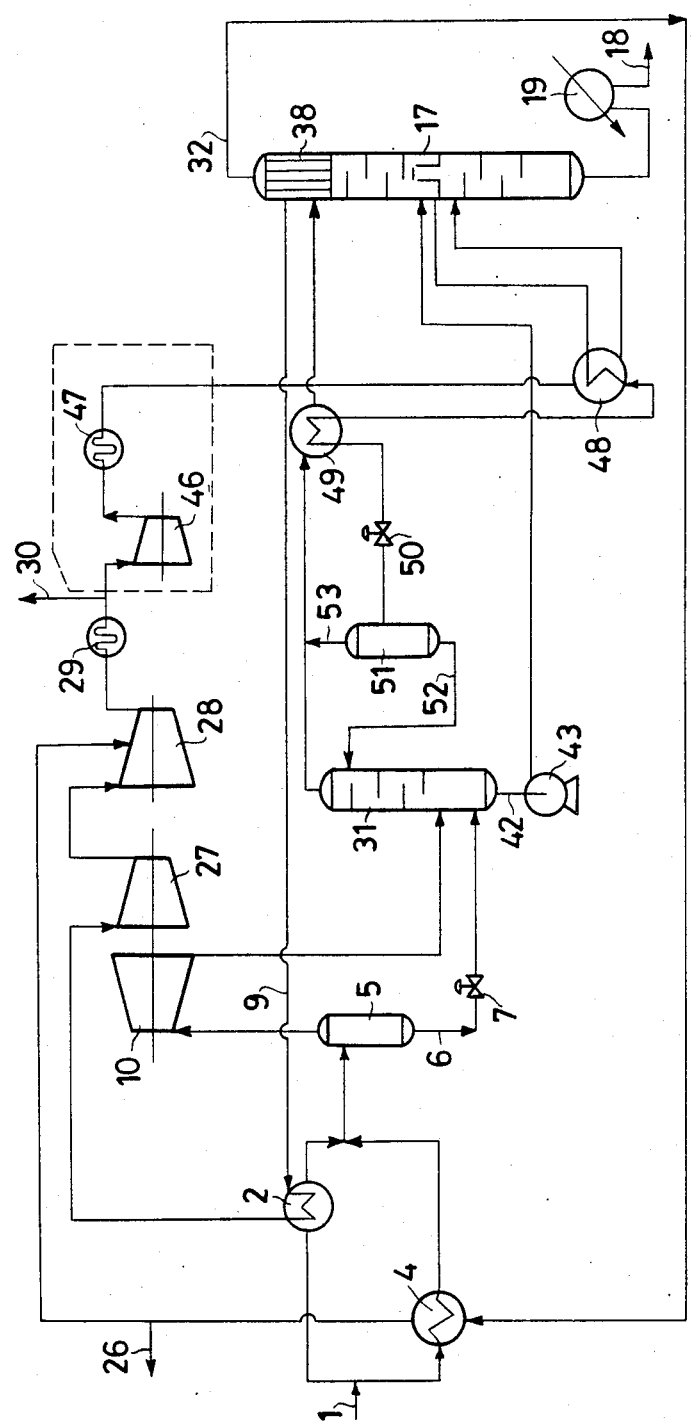

As an example, in FIG. 4 the head gas 32 of the column 17 is heated in the exchanger 4 and fed to a suitable point of the compression unit. The gas to be cooled and partly condensed may be drawn from the delivery of the compressor 28 after the cooling in 29, or after a further compression and cooling in 46 and 47 (enclosed by a dotted line).

The compressed gas is partly condensed in 48 and 49, expanded in 50, sent to the separator 51 wherein a liquid 52, fed to the absorber 31, is separated from the gas 53 which is combined with that outcoming from the absorber 31 (it is obvious that if the compressed gas is at hypercritic pressure, the vapour and the liquid are in reality found only after the expansion in the valve 50).

Figure 5:
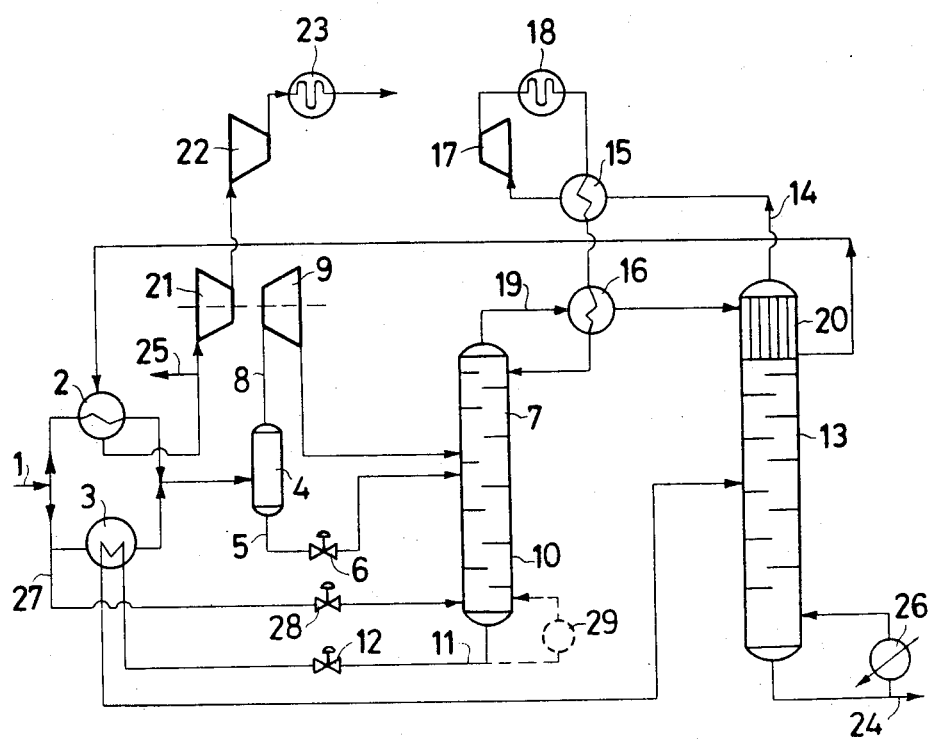

In FIG. 5 the raw gas, previously dehydrated, enters the plant through 1, is cooled by means of process streams in the exchangers 2 and 3 and is sent to the separator 4 separating the condensed liquids 5, which are expanded in 6 and are sent to the separator-absorber 7, and the gas 8, which is expanded in its turn in the turbo-expander 9.

The turbo-expanded gas is fed to the separator-absorber 7 under which a stripping section 10 is provided.

From the bottom of said section a liquid 11 is drawn, the stripped liquid, which is sent through the valve 12 to the fractionation column 13 after having been heated in 3.

In the separator-absorber 7 the turbo-expanded gas is washed in countercurrent by means of a liquid produced by partly condensing the head gases 14 of the column 13 in the exchangers 15 and 16 after having been compressed in 17 and cooled in 18.

From the separator-absorber 7 a gas 19 outcomes which is heated in the exchanger 16, in the dephlegmator 20 of the fractionation column 13 and in the exchanger 2 before being compressed in 21 and 22, cooled in 23 and sent to the distribution network.

The heavy constituents leave the plant by means of the pipe 24, whilst the fuel gas is derived through the pipe 25.

The column 13 is provided with the reboiler 26 and with the dephlegmator 20.

A portion of the entering gas, 27, is used as stripping gas sending it through the valve 28 to the stripping section 10. The stripping may be integrated with the reboiler 29 shown in the figure in dotted line.

As a further exemplifying embodiment, the raw gas may be expanded in a turbo-expander rather than in the valve 28.

The power obtained can be used to the purpose of actuating, either alone, or with the aid of another driving unit, the compressor 17.

In order to better clarifying these possible flowsheets accomplishing the present invention, we report two examples of recovery of heavy constituents.

EXAMPLE 1

Referring to FIG. 2, the raw gas, previously dried, with compositions and flow rates identical to the preceding ones, is cooled in the exchangers 2 and 4 down to $-37°$ C., and is further cooled down to $-61°$ C. by turbo-expansion down to 43.4 kg/cm².

The head product of the column 17, together with the gas developed in the separator 8, after having been compressed and subsequently cooled is partially condensed, producing 409 kmol/h of liquid, which is used as the absorbent oil in the absorber 31. The residual gas is recompressed at 71 kg/cm² after having derived the fuel gas. The heavy hydrocarbons recovered in the liquid state at the bottom of column 17 having the following molar composition:

| | |
|---|---|
| $C_3$ | 39.45 kmol/h |
| $IC_4$ | 38.86 kmol/h |
| $NC_4$ | 44.02 kmol/h |
| $IC_5$ | 21.14 kmol/h |
| $NC_5$ | 15.40 kmol/h |
| $C_6$ | 29.10 kmol/h |
| $C_7$ | 10.89 kmol/h |
| $C_8$ | 5.61 kmol/h |
| $C_9$ | 2.01 kmol/h |
| $C_{10}$ | 0.76 kmol/h |
| Total | 207.24 kmol/h |

The total recovery of butane increases up to 98.34%. The powers used for the recompression of the gas become:

| | |
|---|---|
| Compressor 23 | 904 kW |
| compressor 28 | 4802 kW |
| Total | 5706 kW |

Also in this case, the compressor 27 (1491 kW), driven by the turbo-expander, has not been taken into account.

With the greater recovery of butane a power saving of 29% relatively to the known technique is combined.

EXAMPLE 2

A raw gas previously dehydrated is fed at 35° C. and under 70.3 kg/cm² with compositions and flow rates identical to the preceding ones.

Referring to the flowsheet of FIG. 5, wherein the optional reboiler 29 has not been used, the raw gas is cooled in the exchangers 2 and 3 down to −38° C. and is then further cooled down to −61.5° C. by turbo-expansion down to 43.4 kg/cm².

The head product of the column 13 after having been compressed and subsequently cooled is used as the absorbent oil in the absorber 7.

The residual gas is recompressed up to 71 kg/cm² after having derived the fuel gas. The amount derived in the valve 28 is of 5% relatively to the total raw gas. The heavy hydrocarbons recovered in the liquid state in the bottom of the column 10 have the same molar composition as those of the preceding example, and the total recovery of butane is equally of 98.34%, but the powers used for the recompression of the gas become:

| | |
|---|---|
| Compressor 17 | 407 kW |
| compressor 22 | 4802 kW |
| Total | 5209 kW |

In this case the compressor 21 driven by the turbo-expander, whose power is of 1480 kW, has not taken into consideration.

I claim:

1. Process for the recovery of heavy constituents from a high-pressure hydrocarbon gaseous mixture comprising the following steps:
   (a) cooling and partial condensation of the hydrocarbon gaseous mixture;
   (b) separation of the liquid condensed from the gaseous mixture and feeding of the same liquid to a fractionation column;
   (c) turbo-expansion of non-condensed gaseous mixture;
   (d) separation of the liquid condensed on turbo-expansion of the gaseous mixture and feeding of the same liquid to the said fractionation column, from whose bottom the heavy constituents are recovered;
   (e) recompression both of the gases streaming from the fractionation column and of the gases separated in the step (d), separately or together, up to the consignment pressure of the treated gas,
characterized in that the separation of the liquid condensed on the turbo-expansion of the gaseous mixture is carried out in a separator-absorber in whose lower portion in addition to the condensed liquid a liquid is collected, which is obtained by means of the absorption of non-condensed heavy constituents by means of an absorbent oil constituted by a hydrocarbon liquid, substantially free from the heavy constituents to be recovered, obtained from the cooling and the at least partial condensation of the gases streaming from the fractionation column, previously deprived of at least a portion of the heavy constituents by means of a dephlegmator with which the same fractionation column is provided and compressed to a pressure above that of said fractionation column.

2. Process according to claim 1, wherein the gases streaming from the fractionation column are compressed before being sent to the dephlegmator in order to deprive them of at least a portion of the heavy constituents.

3. Process according to claim 1, wherein the liquid condensed on the turbo-expansion is pumped into the fractionation column at a pressure greater than that of the separator-absorber.

4. Process according to claim 1, wherein the absorbent hydrocarbon liquid is obtained from the cooling and from the at least partial condensation of the gases leaving the fractionation column together with the gases separated in the step (d) at least partly drawn from a suitable point of the recompression unit as per the step (e).

5. Process according to claim 4, wherein the gases at least partly drawn from a suitable point of the recompression unit as per the step (e) are further compressed before being cooled and partly condensed.

6. Process according to claims 4 or 5, wherein the gases at least partly drawn from a suitable point of the recompression unit before being cooled and partly condensed are under a pressure comprised within the range of from 20 to 100 atm, preferably of from 35 to 80 atm.

7. Process according to any one of the claims from 1 to 5, wherein the liquids obtained from the turbo-expansion and from the absorption by hydrocarbon oil are gas-stripped before being sent to the fractionation column.

8. Process according to claim 7, wherein the stripping gas is the raw gas at the plant inlet.

9. Process according to claim 8, wherein the raw gas entering the plant is turbo-expanded before being used as the stripping gas.

10. Process according to claim 9, wherein the power obtained from the turbo-expansion is used, possibly with the aid of another suitable driving unit, for the compression of the head gas of the fractionation column.

11. Process according to claim 8 wherein the stripping gas is in amount of from 2 to 25% by volume of the entering raw gas.

12. Process according to claim 8, wherein at least a portion of the striping gas is replaced by hydrocarbon vapours generated in a reboiler.

13. Process according to claim 7 wherein the stripping gas is in an amount of from 2 to 25% by volume of the entering raw gas.

14. Process according to claim 13, wherein the raw gas entering the plant is turbo-expanded before being used as the stripping gas.

15. Process according to claim 13, wherein at least a portion of the stripping gas is replaced by hydrocarbon vapours generated in a reboiler.

16. Process according to claim 7, wherein at least a portion of the stripping gas is replaced by hydrocarbon vapours generated in a reboiler.

17. Process according to any one of the claims from 1 to 5, wherein the turboexpander outlet pressure and the pressure of the absorber are comprised within the range of from 5 to 70 atm, preferably of from 15 to 50 atm.

18. Process according to any one of the claims from 1 to 5, wherein the pressure of the fractionation column is comprised within the range of from 5 to 45 atm, preferably of from 8 to 35 atm.

* * * * *